United States Patent [19]
Iino et al.

[11] Patent Number: 5,825,500
[45] Date of Patent: Oct. 20, 1998

[54] UNIT FOR TRANSFERRING TO-BE-INSPECTED OBJECT TO INSPECTION POSITION

[75] Inventors: Shinji Iino; Noboru Hayakawa, both of Yamanashi-ken, Japan

[73] Assignee: Tokyo Electron Limited, Japan

[21] Appl. No.: 753,250

[22] Filed: Nov. 21, 1996

[30] Foreign Application Priority Data

Nov. 27, 1995 [JP] Japan ................................... 7-331153

[51] Int. Cl.$^6$ ................................................. G01B 11/00
[52] U.S. Cl. ............................................................ 356/394
[58] Field of Search ................................... 356/394, 244

[56] References Cited

U.S. PATENT DOCUMENTS

| | | | |
|---|---|---|---|
| 5,206,627 | 4/1993 | Kato ......................................... | 250/224 |
| 5,319,216 | 6/1994 | Mokuo et al. ......................... | 250/559.4 |
| 5,331,407 | 7/1994 | Doi et al. ................................ | 356/394 |
| 5,374,147 | 12/1994 | Hiroki et al. ........................... | 414/217 |
| 5,409,348 | 4/1995 | Suzuki ..................................... | 414/416 |

FOREIGN PATENT DOCUMENTS

| | | |
|---|---|---|
| 0 131 466 | 5/1996 | European Pat. Off. . |
| 1-103849 | 4/1989 | Japan . |

Primary Examiner—Frank G. Font
Assistant Examiner—Zandra V. Smith
Attorney, Agent, or Firm—Graham & James LLP

[57] ABSTRACT

A transfer unit according to the invention employs a transfer member movable between a standby position and an inspection position, a detection unit provided at the transfer member for detecting the position of the object on a support surface of the transfer member, a rotatable mount member having a mount surface on which the object is mounted, and capable of transferring the object between the mount surface and the support surface of the transfer member, and a control unit for calculating an amount of deviation of the object from a reference position on the basis of a detection value of the detection unit, the control unit also driving the mount member and the transfer member to correct the amount of deviation of the object from the reference position on the basis of the calculation result.

11 Claims, 7 Drawing Sheets

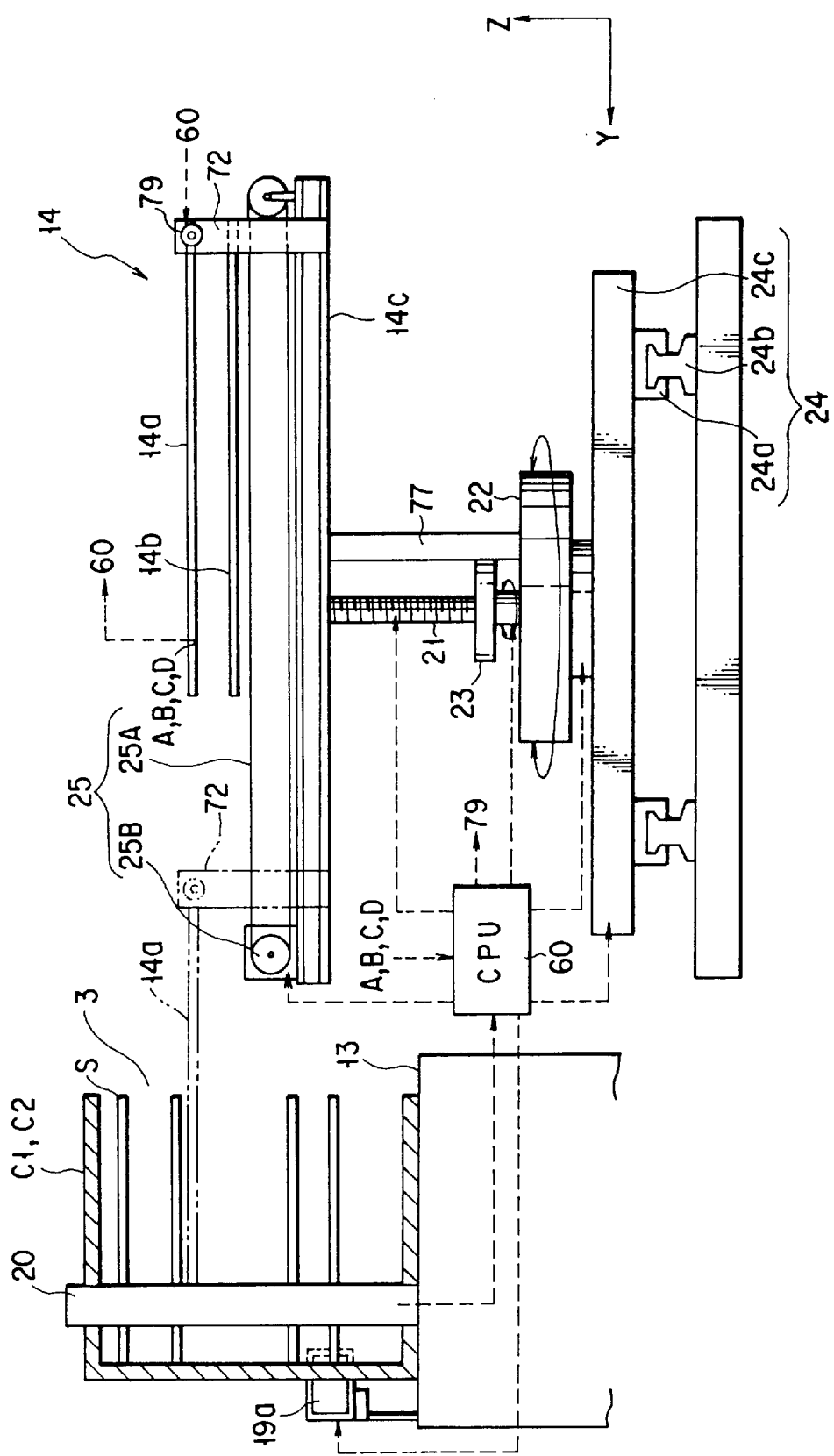
F I G. 2

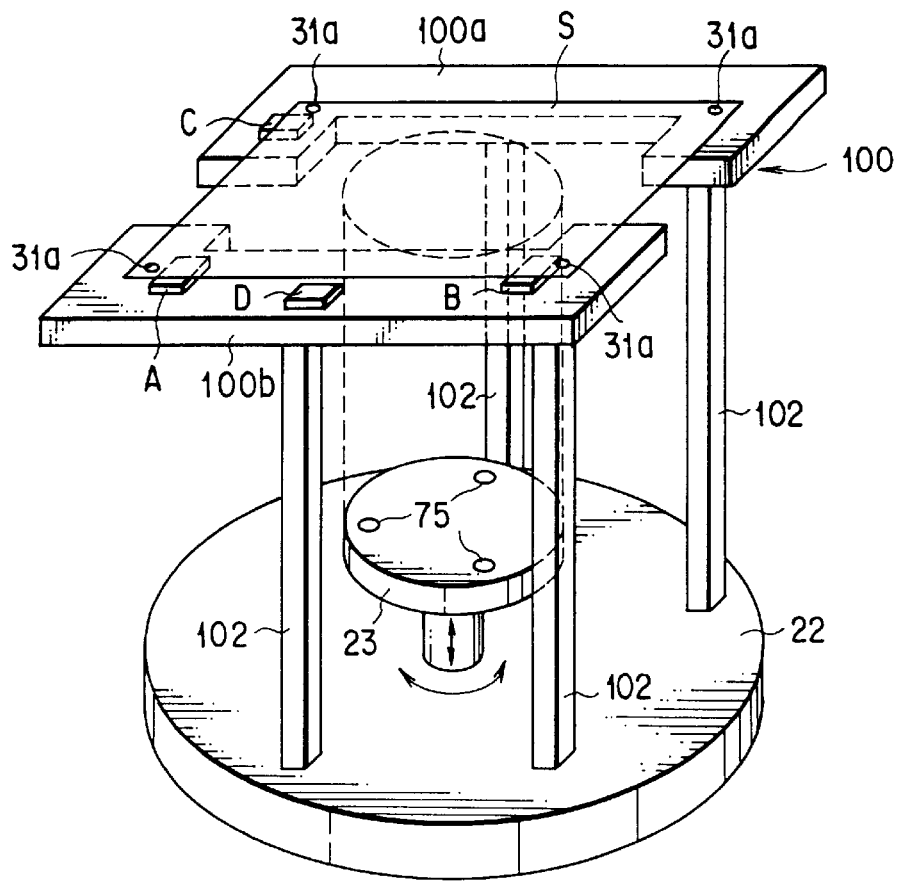
F I G. 8
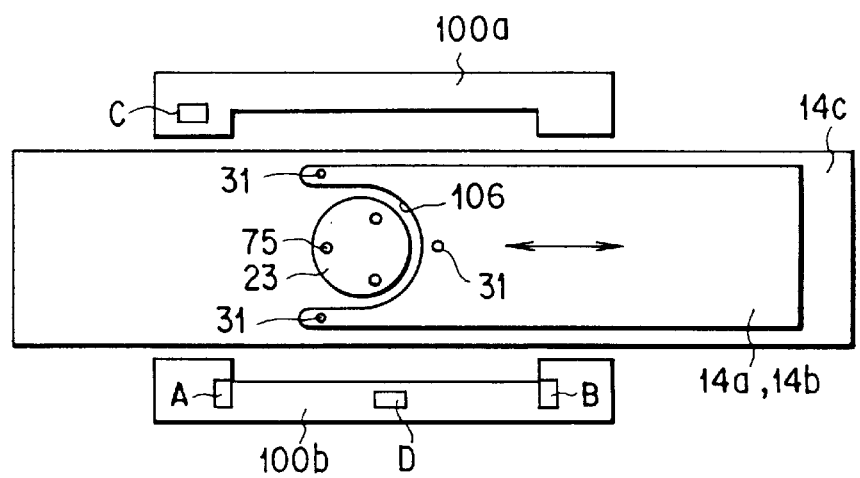
F I G. 9

UNIT FOR TRANSFERRING TO-BE-INSPECTED OBJECT TO INSPECTION POSITION

BACKGROUND OF THE INVENTION

1. Field of the Invention

This invention relates to a unit for transferring a to-be-inspected object to an inspection position.

2. Description of the Related Art

A probe apparatus for inspecting electric characteristics, for example, of an LCD (Liquid Crystal Display) substrate is known as an inspection apparatus for performing predetermined inspection of an object such as an LCD substrate for an LCD or a semiconductor wafer. A technique concerning the probe apparatus is disclosed e.g. in Japanese Patent Application KOKAI Publication No. 63-311390. This publication discloses a method for testing an LCD substrate of an active matrix structure, and a technique employed in the method.

In the case, for example, of an LCD of a TFT type, a glass substrate provided with a plurality of electric circuits for performing ON/OFF control of each pixel is generally used as the LCD substrate. The electric circuits are produced in the form of a matrix on the LCD substrate (glass substrate) by means of a film-forming apparatus, etc. A great number of electrode pads serving as electric contacts are provided around the electric circuits arranged in the form of a matrix. At the time of electric inspection for determining whether or not each electric circuit is in a normal state, the LCD substrate is situated in a predetermined position, and electrode pads located on peripheral portions of the LCD substrate are brought into electric contact with probes employed in the probe apparatus, to inspect the electric characteristics of the substrate. To this end, it is necessary to use a transfer unit for accurately detecting the present position of the LCD substrate, and accurately transferring the substrate to an inspection position after situating it, on the basis of the detection result, in a reference position corresponding to the inspection position.

Such a transfer unit is generally employed in a probe apparatus for inspecting LCD substrates. The position detection of the LCD substrate by the transfer unit is performed by applying light to an LCD substrate placed on a mount table from below, and detecting light reflected from the corners thereof. Since a mechanism for detecting the position of the LCD substrate is provided at only a single place, it is necessary to rotate the LCD substrate placed on the mount table in order to detect the corners. In the case, for example, of detecting the position of a large and thin LCD substrate with a size of 550 mm (length) ×650 mm (width) ×0.7 mm (thickness), a greater part of the LCD substrate will project from the mount table, and hence may greatly deform or have an edge portion thereof bent upward or downward during position detection. As a result, the position of the large and thin LCD substrate may be deviated from a correct position and accordingly be hard to accurately detect. Moreover, if the LCD substrate is still thinner, detection data obtained by radiating the LCD substrate with light will be greatly influenced by disturbance light from the outside, with the result that the accurate position of the LCD substrate will not be detected.

SUMMARY OF THE INVENTION

It is the object of the invention to provide an apparatus capable of accurately detecting the position of an object such as an LCD substrate, irrespective of its size, thickness or detection state, and accurately transferring the substrate to an inspection position after situating the substrate in a reference position which is aligned with the inspection position.

To attain the object, there is provided a transfer unit comprising: at least one transfer member movable between a standby position in which an object is in a standby state, and an inspection position in which the object is inspected, and having a support surface on which the object is mounted; first fixing means provided at the support surface of the transfer member for fixing the object on the support surface; detection means provided at the transfer member for detecting the position of the object on the support surface; a rotatable mount member having a mount surface on which the object is mounted, and capable of transferring the object between the mount surface and the support surface of the transfer member; second fixing means provided at the mount surface of the mount member for fixing the object on the mount surface; and control means for calculating an amount of deviation of the object from a reference position on the basis of a detection value of the detection means, with the object held on the support surface of the transfer member by means of the first fixing means, the control means also driving the mount member and the transfer member to correct the amount of deviation of the object from the reference position on the basis of the calculation result, with the object held on one of the support surface of the transfer member and the mount surface of the mount member by means of a corresponding one of the first and second fixing means, thereby situating the object in the reference position.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate a presently preferred embodiment of the invention and, together with the general description given above and the detailed description of the preferred embodiment given below, serve to explain the principles of the invention.

FIG. 2 is a side view, showing an essential part of the LCD substrate inspection apparatus of FIG. 1;

FIG. 8 is a perspective view, showing an essential part of the LCD substrate inspection apparatus of FIG. 7; and FIG. 9 is a plan view, showing an essential part of the LCD substrate inspection apparatus of FIG. 7.

DETAILED DESCRIPTION OF THE PREFERRED EMBODIMENT

The embodiment of the invention will be described with reference to the accompanying drawings.

Figure 1:
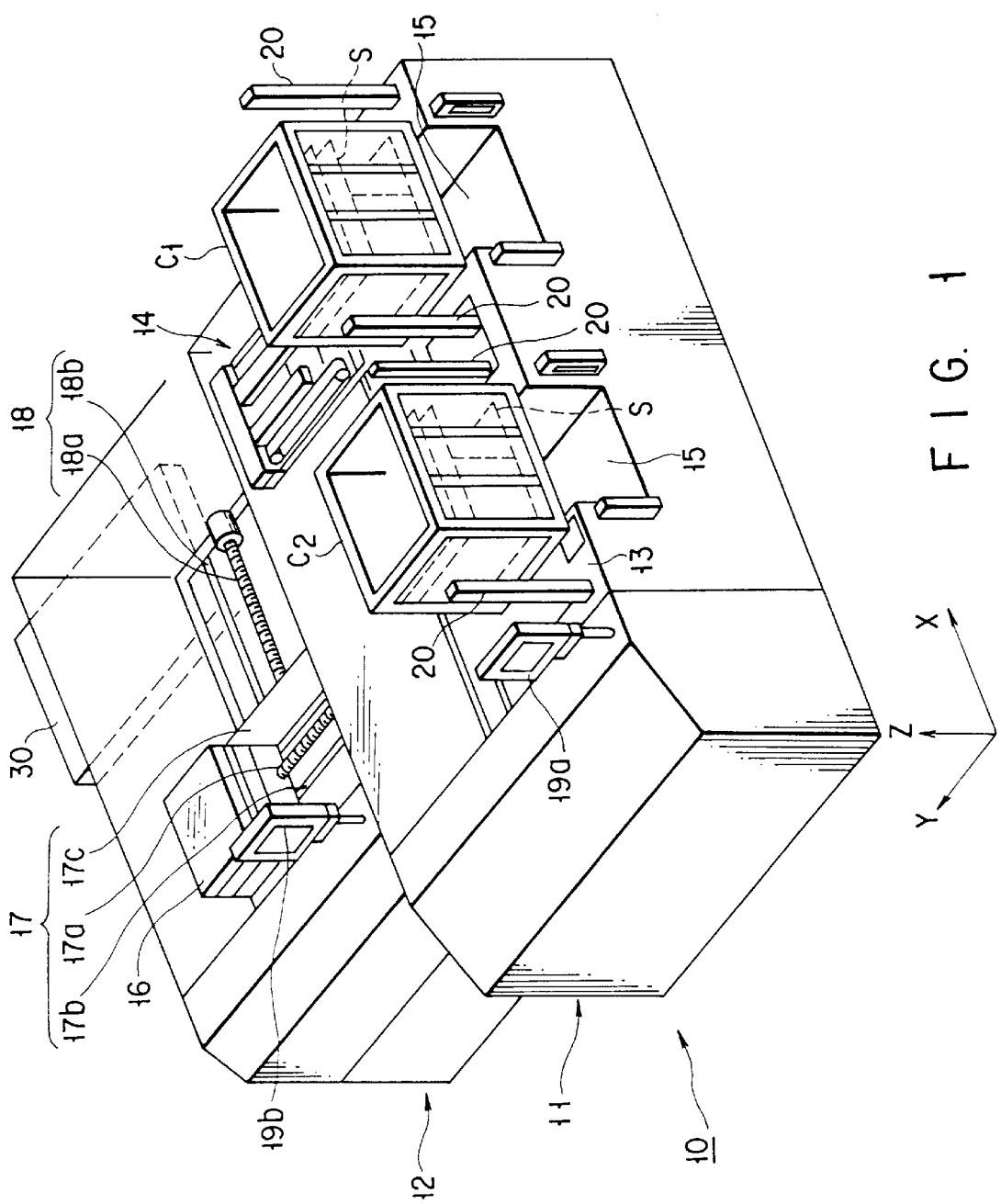
FIG. 1 is a perspective view, showing an LCD inspection apparatus according to the embodiment of the invention.

As is shown in FIG. 1, a probe apparatus 10 as an inspection apparatus for inspecting an LCD substrate S comprises a loader section 11 for loading and unloading the LCD substrate S which consists of a rectangular glass substrate with a size of 550 mm (length) ×650 mm (width) ×0.7 mm (thickness), and a probe section 12 for electrically inspecting the LCD substrate S transferred from the loader section 11.

As is shown in FIGS. 1 and 2, a plurality of containers, e.g. cassettes C1 and C2, can be mounted on a predetermined section (i.e. cassette mounting section 13) of the loader 11. Each of the cassettes C1 and C2 can contain a predetermined number (e.g. 25) of LCD substrates S such that they are piled on each other at regular intervals in a predetermined direction (in the Z-axis direction in FIG. 1). The interval between each pair of adjacent substrates is set so that arms 14a and 14b (see FIG. 2), described later, incorporated in a transfer unit (transfer means) 14 for transferring each LCD substrate can be inserted therein (just below the reverse surface of the substrate). The cassettes C1 and C2 are arranged parallel to each other in a predetermined direction of the loader section 11 (in the X-axis direction in FIG. 1). For example, the cassette C1 contains LCD substrates S to be inspected, while the cassette C2 contains LCD substrates S having been inspected. The transfer unit 14 is arranged movable and opposed to the cassettes C1 and C2, for taking, one by one, the to-be-inspected LCD substrates S from the cassette C1, then transferring them to the probe section 12, then receiving from the probe section 12 the LCD substrates S having been inspected, and transferring them to the cassette C2.

Two detection units 20 are provided opposed to opposite side surfaces of the cassette C1, respectively, (i.e. the cassette C1 is interposed between the detection units 20) for cooperating with each other to detect whether one or more LCD substrates S remain in the cassette C1. Specifically, one of the two detection units 20 has a light emission element, and the other has a light receiving element. When light emitted from the light emission element is received by the light receiving element, a detection signal (electric signal) is generated from the light receiving element to a CPU 60 (see FIG. 2). On the basis of the electric signal, the CPU 60 determines whether one or more LCD substrates S remain in the cassette C1, or where in the cassette C1 the next substrate S is situated, and then displays a determination result on a liquid crystal panel 19a. As in the case of the cassette C1, two detection units 20 are provided opposed to opposite side surfaces of the cassette C2, respectively, for cooperating with each other to detect whether one or more LCD substrates S remain in the cassette C2. These four detection units 20 are arranged substantially in line in a predetermined direction (in the X-axis direction in FIG. 1).

As is shown in FIG. 2, each of the cassettes C1 and C2 has an opening 3 opposed to the transfer unit 14 for permitting the LCD substrates S to be taken therefrom or received therein. A plurality of support grooves (not shown) are formed in the inner side surfaces of each of the cassettes C1 and C2 for horizontally supporting the LCD substrates S at regular intervals in the vertical direction. Further, as is shown in FIG. 1, recesses 15 are formed in the loader section 11 for respectively permitting the cassettes C1 and C2 to be automatically set on the cassette mount section 13. More specifically, each recess 15 has a size which permits the robot hand of an automatic transfer vehicle (AGV) developed in accordance with automation of the inspection, to be inserted therein. The automatic transfer vehicle transfers each cassette C1 or C2 between process units in a clean room, and automatically sets it on the cassette mount section 13 of the loader section 11 by inserting the robot hand into the recess 15. The transfer of the cassettes C1 and C2 by the automatic transfer vehicle is controlled by a host computer (not shown).

Referring again to FIG. 1, the probe section 12 includes a mount table 16 for mounting thereon the LCD substrate S, a Y-directional movement mechanism 17 for moving the mount table 16 in the Y-axis direction, and an X-directional movement mechanism 18 for moving the mount table 16 in the X-axis direction. The Y-directional movement mechanism 17 comprises, for example, a main body 17c which has a ball screw 17a engaged with the mount table 16 and extending in the Y-axis direction, and a rail guide 17b engaged with the mount table 16 for guiding the table 16 in the Y-axis direction. The X-directional movement mechanism 18 comprises, for example, a ball screw 18a engaged with the main body 17c of the Y-directional movement mechanism 17 and extending in the X-axis direction, and a rail guide 18b engaged with the main body 17c for guiding the main body 17c in the X-axis direction.

The probe section 12 also includes an inspection section 30 with probes to be brought into contact with a train of electrodes provided on a peripheral portion of the LCD substrate S. At the time of inspecting the LCD substrate S mounted on the mount table 16, the probes of the inspection section 30 are brought into contact with the electrodes arranged in line on the substrate, and electric inspection signals are transmitted from a tester (not shown) to LCD driving circuits (not shown) incorporated in the LCD substrate S.

The liquid crystal display panel 19b is provided in the vicinity of the mount table 16. The panel 19b is used to set various inspection items at the time of inspecting the LCD substrate S, or to display, using a predetermined control program, on which portion of the probe apparatus 10 the LCD substrate S is situated.

Figure 3:
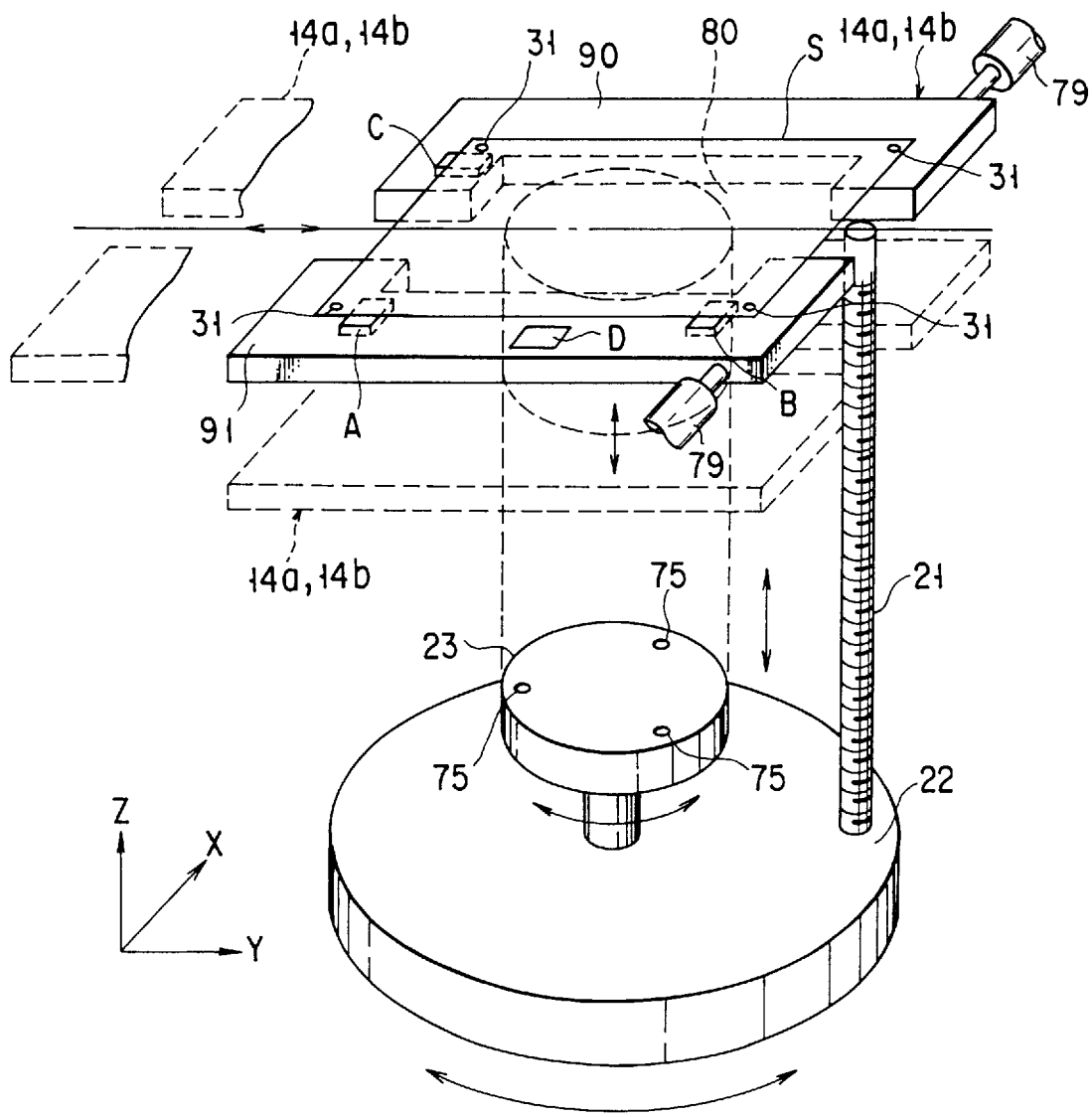
FIG. 3 is a perspective view, showing an essential part of the LCD substrate inspection apparatus of FIG. 1.

Referring then to FIGS. 2 and 3, the transfer unit 14 will be described in detail.

The transfer unit 14 has a plurality of arms, for example, the load arm 14a and unload arm 14b, in order to simultaneously perform a load operation to take a to-be-inspected LCD substrate S from the cassette C1 and transfer it to the probe section 12, and an unload operation to receive an inspected LCD substrate S from the probe section 12 and transfer it to the cassette C2. The load arm 14a and the unload arm 14b extend parallel to each other in the vertical direction, and can horizontally advance and retreat over a support table 14c, independent of each other. As is shown in FIG. 3, each of the arms 14a and 14b comprises a pair of arm portions 90, 91, which can cooperate to form an opening 80 for permitting a mount member 23 (which will be described later) to move therethrough in the vertical direction. In FIG. 3, the support table 14c is not shown.

To individually move the arms 14a and 14b in the horizontal direction, advancing/retreating mechanisms 25 for driving the arms 14a and 14b, respectively, are provided on the support table 14c. In FIG. 2, only one of the mechanisms 25 is shown. Each of the advancing/retreating mechanisms 25 comprises a timing belt 25A secured to a coupling member 72 fixed to a corresponding one of the arms 14a and 14b, a rotary roller 25B for rotating the timing belt 25A, and a guide rail (not shown) engaged with the coupling member 72 to guide it (and accordingly the arm 14a or 14b) in the Y-axis direction. The rotary roller 25B is controlled by the CPU 60.

The coupling member 72 has two support portions for respectively supporting the arm portions 90 and 91. Each of the support portions is coupled with a cylinder 79. As shown in FIG. 3, the cylinder 79 have expand/contract rods fixed to the arm portions 90 and 91, respectively. Expanding or contracting the rods of the cylinders varies the X-directional distance between the arm portions 90 and 91, such that the arm 14a or 14b can be inserted into the space between each pair of adjacent LCD substrates S contained in the cassette C1 or C2, and also such that the opening 80 for passing therethrough the mount member 23 can be defined between the arm portions 90 and 91. The support surfaces of the arms 14a and 14b for supporting an LCD substrate S consist of the upper surfaces of the arm portions 90 and 91.

The support surface of each arm 14a or 14b, on which the LCD substrate S is mounted, has a plurality of suction holes 31 formed therein for holding the substrate S on the support surface by a predetermined suction force, as is shown in FIG. 3. The suction holes 31 are formed in predetermined portions of the support surface of each arm 14a or 14b, for example, in four corner portions on which the substrate S is mounted.

The support table 14c which supports the arms 14a and 14b is engaged with a vertically extending ball screw 21, and is disposed to move in the vertical direction (i.e. in the Z-axis direction) in accordance with the rotation of the ball screw 21. A rail guide 77 is engaged with the support table 14c such that the table 14c can move vertically without rotation in accordance with the rotation of the ball screw 21. The ball screw 21 has its lower end attached to a base table 22 located below the support table 14c such that it can rotate relative to the base table 22. The rail guide 77 has a lower end portion fixed to the base table 22. The base table 22 is disposed to rotate about its axis of rotation extending in the Z-axis direction, so that the LCD substrate S can be transferred between the cassette C1 or C2 and the probe section 12 by rotating the arm 14a or 14b.

A mount member 23 is placed on the base table 22 such that it can rotate, relative to the table 22, about its axis of rotation extending in the Z-axis direction (in a direction of θ), and can move in the vertical direction. The LCD substrate S taken out of the cassette C1 by the arm 14a is temporarily mounted on the support surface of the mount member 23 before being transferred to the probe section 12, and is rotated for accurate positioning. The mount member 23 has a plurality of suction holes 75 (see FIG. 3) formed therein for holding the LCD substrate S thereon by a predetermined suction force.

The base table 22 is moved by an X-directionally driving mechanism 24 so that a to-be-inspected LCD substrate S can be transferred from the cassette C1 to the probe section 12 by the arm 14a, and an inspected LCD substrate S can be transferred from the probe section 12 to the cassette C2 by the arm 14b. The X-directionally driving mechanism 24 comprises a movable member 24c supporting the base table 22, a guide rail 24b extending on the overall surface of the loader section 11 in the X-axis direction, and an engagement claw 24a secured to the lower surface of the movable member 24c and engaged with the guide rail 24b.

The vertical level of the arms 14a and 14b at the time of transfer of the LCD substrate S is set to a predetermined value by means of the CPU 60. By virtue of the level control, the LCD substrate S is prevented, at the time of being transferred to and from the cassettes C1 and C2, from interfering with the other LCD substrates contained in the cassettes C1 and C2.

The ball screw 21, the base table 22, the mount member 23, the X-directionally driving mechanism 24 and the cylinders 79 are controlled by the CPU 60.

Figure 4:
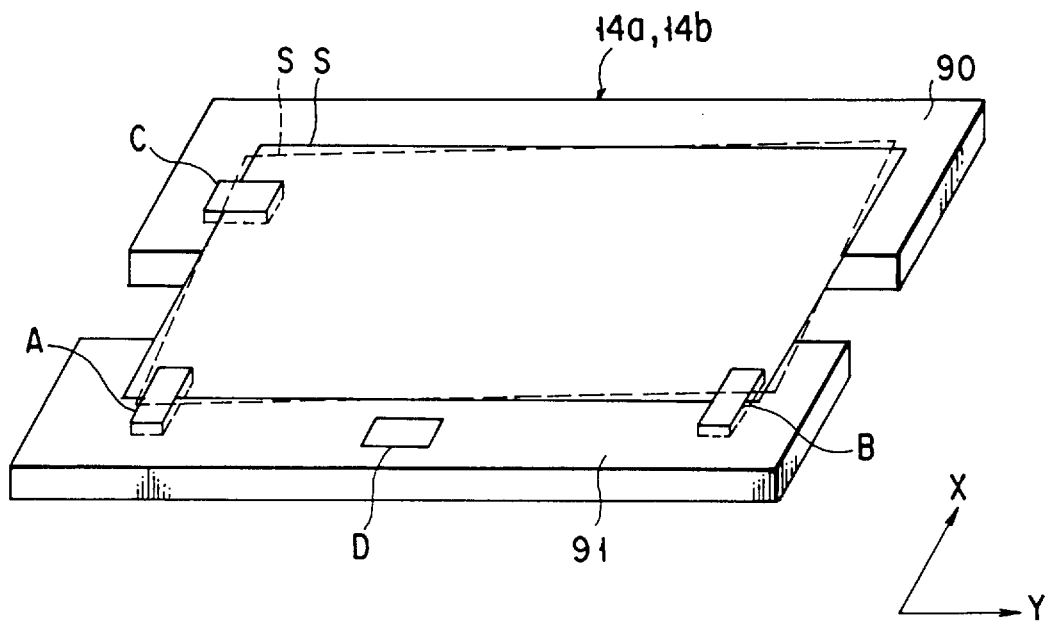
FIG. 4 is a schematic enlarged perspective view, showing an arm appearing in FIG. 3.

As is shown in FIG. 3, the substrate-supporting surface of each of the arms 14a and 14b is equipped with a detection mechanism for detecting the position of the LCD substrate S placed thereon. The detection mechanism comprises a line sensor consisting of a plurality of detection elements or cells 34 (see FIG. 5) with a size of 10–50 microns, preferably 25 microns, each of which can detect the position of a fine portion of the substrate S. As is shown in FIG. 4, this embodiment employs three line sensors A, B and C on three peripheral portions of the substrate-mounting area of the support surface of each arm 14a, 14b. Basically, the line sensors A, B and C detect the position of the LCD substrate S by detecting room light applied thereto and reflected therefrom (the position correction of the LCD substrate S based on the position detection will be described later).

The line sensors A, B and C are, for example, received in recesses formed in the support surface of each arm 14a, 14b. Thus, the LCD substrate S is kept out of contact with the line sensors A, B and C, thereby minimizing the detection error. Preferably, the optical system constituting the line sensors is constructed such that it restrains scattering light generated from the interior of the translucent LCD substrate S and can detect only the reverse surface thereof.

Figure 6:
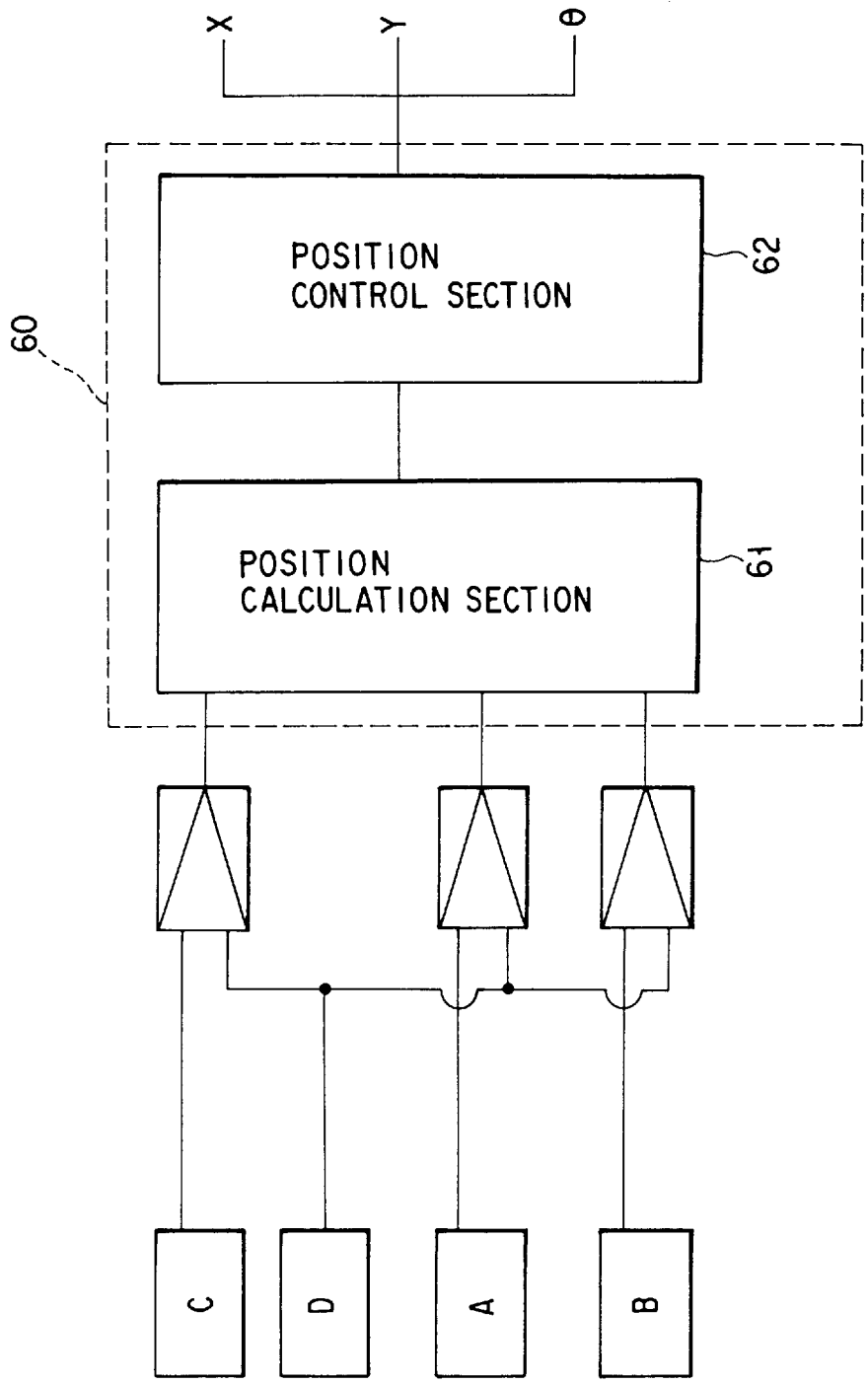
FIG. 6 is a block diagram, showing a detection control system incorporated in the LCD substrate detection apparatus of FIG. 1.

A detection signal generated from each cell 34 of the line sensors A, B and C and indicating the position of a fine portion of the LCD substrate S is supplied as data signal to a position calculation section 61 (see FIG. 6) incorporated in the CPU 60. For example, pulse signals respectively output from the cells 34, with addresses assigned thereto, of the line sensors A, B and C are supplied as position data items to the position calculation section 61 of the CPU 60. When the position of the LCD substrate S is calculated, an alignment operation is performed to correct positional deviation of the substrate S from a predetermined reference position on the basis of a calculation result. This alignment operation is performed under the control of a position control section 62 (see FIG. 6) incorporated in the CPU 60. Specifically, the calculation result of the position calculation section 61 is supplied to the position control section 62, which, in turn, drives the arms 14a and 14b, the ball screw 21 and the mount member 23 in a manner described later, thereby correcting the X-directional deviation, the Y-directional deviation and the angular deviation (in the direction of θ) of the LCD substrate S.

To keep constant the background of detection assumed at the time of detecting the position of the LCD substrate S, a disturbance light-detecting cell D is provided on the support surface of each of the arms 14a and 14b. At the time of the position detection, the position calculation section 61 inputs, as data, disturbance light detected by the disturbance light-detecting cell D, and determines the amounts of light to be detected by the line sensors A, B and C in accordance with variations in disturbance light. In other words, the position calculation section 61 corrects the detection values of the line sensors A, B and C on the basis of the detection value of the disturbance light-detecting cell D.

To obtain the position data of the LCD substrate S, the position calculation section 61 may take data only from those of the cells 34 which have received light reflected from the LCD substrate S. Alternatively, the section 61 may check whether there is light reflected from the LCD substrate S, concerning all the cells 34 in sequence of address. In the latter case, it may be constructed such that if there is reflection light, an H (high) signal is output, and if there is no reflection light, an L (low) signal is output, thus obtaining the data items of all the cells 34 and determining the position of the LCD substrate S on the basis of the data items.

The operation of the probe apparatus 10 constructed as above will now be described.

When the probe apparatus 10 is turned on, the transfer unit 14 takes one of the LCD substrates S from the cassette C1 in accordance with a predetermined program, and transfers the substrate to the probe section 12. This transfer operation will be described in more detail.

As is shown in FIG. 1, the transfer unit 14 is moved by the X-directional movement mechanism 24 to a position opposed to the cassette C1 which contains to-be-inspected LCD substrates S. At this time, the base table 22 is rotated, and the load arm 14a is set in a direction (see FIG. 2) in which it can take an LCD substrate S from the cassette C1. Thereafter, the load arm 14a is raised to a predetermined level in accordance with the rotation of the ball screw 21, and the distance between the arm portions 90 and 91 is set to a predetermined valve by moving the cylinders 79. Then, the arm 14a is forwarded by means of the advancing/retreating mechanism 25 to a predetermined position just below that one of the LCD substrates S which should be inspected now. Then, the arm 14a is raised by a predetermined amount, whereby the to-be-inspected LCD substrate S is placed on the support surface of the arm 14a. The upward movement of the arm 14a is stopped in a position in which the to-be-inspected LCD substrate S does not interfere with another LCD substrate located just above it. Subsequently, the arm 14a is retreated by the advancing/retreating mechanism 25, thereby taking the substrate out of the cassette C1. During transfer, the position of the substrate is detected by the line sensors A, B and C provided on the arm 14a. Thus, the distance between the arm portions 90 and 91 of the arm 14a is set as shown in FIG. 3, after it takes the LCD substrates S completely out of the cassette C1. In other words, the arm portions 90 and 91 are X-directionally moved to a position in which peripheral portions of the LCD substrates S can be detected by the line sensors A, B and C. Thereafter, the LCD substrate S is temporarily held on the support surface of the arm 14a by a suction force through the suction holes 31 formed in the support surface. In a state in which the substrate is temporarily held, position detection is performed. As described above, the x-directional movement of the arm portions 90 and 31 after taking the LCD substrate S from the cassette C1 by the load arm 14a is performed with the LCD substrate S raised by the mount member 23 above the support surface of the arm 14a.

Figure 5:
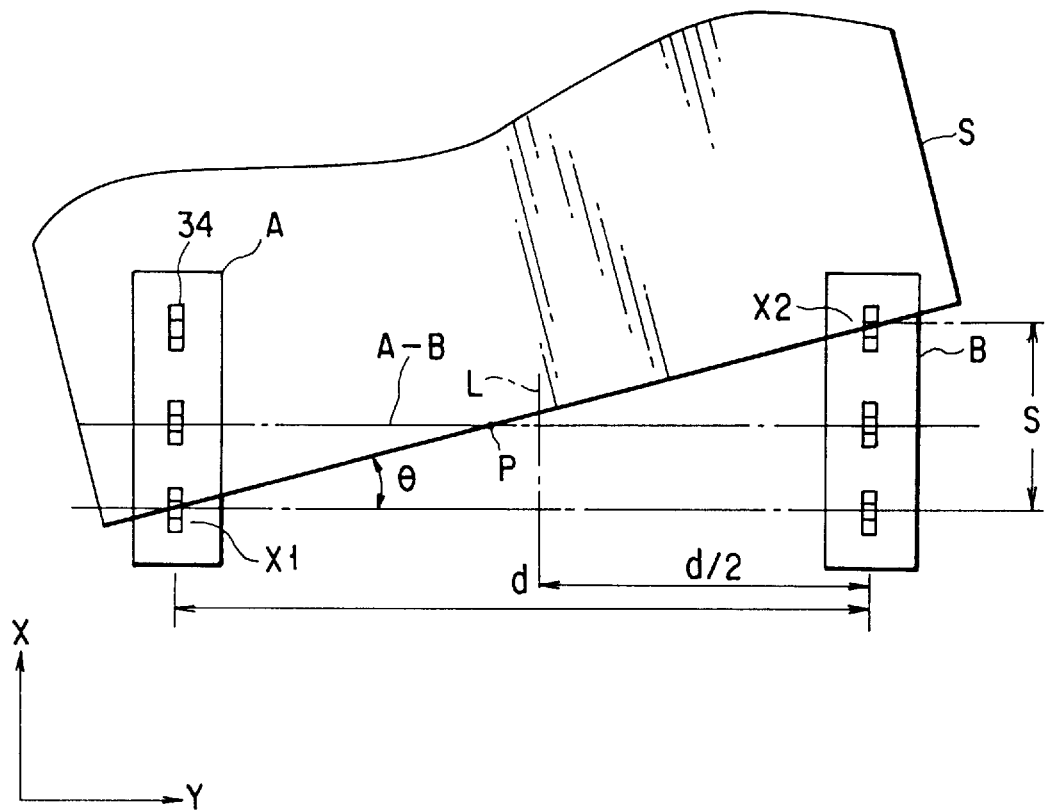
FIG. 5 is a view, useful in explaining position correction of the LCD substrate on the arm.

The detection of the position of the LCD substrate S by the line sensors A, B and C, and an alignment operation based on the detection result for correcting positional deviation of the substrate from a predetermined reference position (which corresponds to the inspection position) will be described in detail with reference to FIGS. 4 and 5.

As aforementioned, three portions of the LCD substrate S temporarily held on the load arm 14a are detected during transfer by the line sensors A, B and C located at predetermined peripheral portions of the support surface of the arm 14a. First, the inclination angle θ of the LCD substrate S in the Y-axis direction, which is a parameter indicative of the amount of deviation, is calculated on the basis of position data concerning the substrate and obtained by the two line sensors A and B arranged in the Y-axis direction, and a predetermined distance d between the line sensors A and B. For example, where the line sensors A, B and C have a size of 25 μm, the amount of X-directional deviation s of the LCD substrate S is expressed by |x2−x1|×25 [μm ] on the basis of the position of the x1-th cell 34 of the line sensor A and the position of the x2-th cell 34 of the line sensor B (the x1-th cell 34 and the x2-th cell 34 are situated in boundary areas in which reflection light is found). From the deviation amount s and the predetermined distance d between the line sensors A and B, the Y-directional inclination angle θ of the LCD substrate S is given by $$\theta = \tan^{-1}\{|x2-x1| \times 25 \,[\mu m] \times 1/d\}$$

If the accuracy of alignment is 100 μm, θ=0.019°.

To correct the thus-obtained inclination angle θ of the LCD substrate S in the Y-axis direction, first, the LCD substrate S is mounted on the mount member 23. To mount the substrate on the mount member 23, the load arm 14a and the mount member 23 are moved relative to each other in the Z-axis direction so that they approach each other, whereby the support surface of the arm 14a and the support surface of the mount member 23 are situated at the same level as indicated by the broken line in FIG. 3. At this time, the support surface of the mount member 23 is situated in the opening 80 of the load arm 14a, and is brought into contact with the reverse surface of the LCD substrate S placed on the support surface of the arm 14a. In the above-mentioned relative Z-directional movement, it is desirable to move only the mount member 23 in the Z-axis direction in order to lessen the shock exerted on the LCD substrate S when it is mounted on the mount member 23.

After the reverse surface of the LCD substrate S contacts the support surface of the mount member 23, the substrate is transferred from the load arm 14a to the mount member 23. At this time, so as not to displace the position of the substrate, the substrate is attracted to the mount member 23 by a suction force through the suction holes 75, with its corner portions held to the support surface of the arm 14a by a suction force through the suction holes 31. Thereafter, the suction force on the side of the arm 14a is released. After a series of suction operations are completed, the load arm 14a and the mount member 23 are separated from each other. In other words, the mount member 23 is raised in the Z-axis direction. Then, the mount member 23 is rotated together with the substrate by a deviation angle θ calculated from the position detection value concerning the substrate S, thereby situating the substrate S in a predetermined position.

After finishing the correction of the deviation angle θ, the X-directional deviation and the Y-directional deviation of the LCD substrate S are corrected. Specifically, after the correction of the deviation angle θ, the mount member 23 and the load arm 14a are moved to approach each other (for example, the load arm 14a is raised up to the mount member 23). When the support surfaces of the mount member 23 and the load arm 14a are situated at the same level, the Y-directional center portion of the load arm 14a is aligned with that of the mount member 23. Thus, the Y-directional deviation of the LCD substrate S is corrected. In this deviation correction, the load arm 14a is moved by the advancing/retreating mechanism such that an intersection P between the outline of the LCD substrate S and an imaginary line A-B passing the center points of the line sensors A and B is situated on the vertical bisector L of the line A-B. After the Y-directional positioning, the LCD substrate S is transferred from the mount member 23 to the load arm 14a by the above-described sequential suction operations.

Thereafter, to correct the X-directional deviation of the LCD substrate S, the substrate is again mounted on the mount member 23. In this state, the X-directional correction is performed in the same manner as employed to perform the Y-directional correction, on the basis of the position data concerning the LCD substrate S obtained by the line sensors A and C. In this case, however, the mount member 23 is rotated through 90° with the LCD substrate S mounted thereon, and the load arm 14a is advanced and retreated in the same manner as in the Y-directional correction to perform the X-directional correction. After the X-directional correction or positioning, the LCD substrate S is transferred from the mount member 23 to the load arm 14a by the above-described sequential suction operations. As a result of the angular (θ) correction and the X- and Y-directional correction, the LCD substrate S is accurately situated in the reference position (which is aligned with the inspection position).

The LCD substrate S accurately situated in the reference position is transferred toward the inspection position in the probe section 12 by the load arm 14a of the transfer unit 14. The transfer unit 14 approaches the mount table 16 in the probe section 12, with the load arm 14a set at a predetermined level, and then forwards the load arm 14a by means of the advancing/retreating mechanism 25, thereby positioning the arm 14a with the LCD substrate S just above the mount surface of the mount table 16. In this state, support pins (not shown) are raised from the mount table 16, thereby supporting the substrate S above the support surface of the load arm 14a. Subsequently, the load arm 14a is retreated therefrom by the advancing/retreating mechanism 25, and the support pins are lowered to place the substrate S on the mount table 16.

The LCD substrate S placed on the mount table 16 is held thereto by means of a suction mechanism (not shown). The alignment of the LCD substrate S with the inspection position is performed by recognizing, using recognition means (not shown), an alignment mark (as a reference mark) formed on a predetermined portion of the substrate S, and situating the alignment mark in a predetermined reference position. Similarly, positioning of the inspection section 30 is performed by recognizing, using recognition means (not shown), an alignment pin (reference pin) provided on the probe section 12.

The LCD substrate S situated in the predetermined inspection position has its peripheral electrodes brought into electric contact with the probes of the inspection section 30, and receives predetermined electric signals from a tester (not shown). Thus, the electric characteristics of the LCD substrate S are inspected. Specifically, it is inspected in accordance with the program stored in the CPU 60 whether the substrate S is defective or what a quality it has. After the inspection, the transfer unit 14 transfers the LCD substrate S from the probe section 12 to the loader section 11, and then into the cassette C2 in the cassette mount section 13. The above-described inspection is sequentially repeated until all the to-be-inspected LCD substrates S contained in the cassette C1 are inspected. Alternatively, it may be constructed that only voluntary ones of the LCD substrates contained in the cassette C1, instead of all the substrates S, are inspected in accordance with a predetermined program stored in the CPU 60.

As described above, in the transfer unit 14 of the probe apparatus 10 of the invention, the position of the LCD substrate S, as an object to be transferred, is detected while the substrate is reliably held on the support surface (mount surface) of the arm 14a or 14b by a suction force. Accordingly, an error in position detection due to the physical vibration or the configuration of the LCD substrate S is restrained, with the result that the positioning accuracy of the substrate is enhanced.

Further, in the transfer unit 14 of the invention, at the time of transferring the LCD substrate S between the mount member 23 and the arm 14a or 14b, that one of the mount member 23 and the arms 14a or 14b which holds the substrate thereon is stopped, while the other of the mount member 23 and the arms 14a or 14b is moved. Therefore, the substrate can be prevented from being damaged because of its weight when it is transferred, and also the already positioned substrate can be prevented from being displaced.

Moreover, since in the transfer unit 14 of the invention, the position of the LCD substrate S is detected on the arm 14a when the substrate is transferred from the cassette C1, the conventional process step of transferring the substrate to the mount member 23 to detect its position is omitted, thereby enhancing the throughput.

In addition, in the transfer unit 14 of the invention, in order to keep constant the background of detection assumed at the time of detecting the position of the LCD substrate S, the disturbance light-detecting cell D is provided on the support surface of each of the arms 14a and 14b for determining the amounts of light to be detected by the line sensors A, B and C in accordance with variations in disturbance light. In other words, the detection values of the line sensors A, B and C are corrected on the basis of the detection value of the disturbance light-detecting cell D, so that the detection values of the line sensors A, B and C will not be influenced by disturbance light. Accordingly, even if the LCD substrate S is thin and translucent or if the amount of ambient light varies, the position of the substrate can be optically detected with high accuracy.

Figure 7:
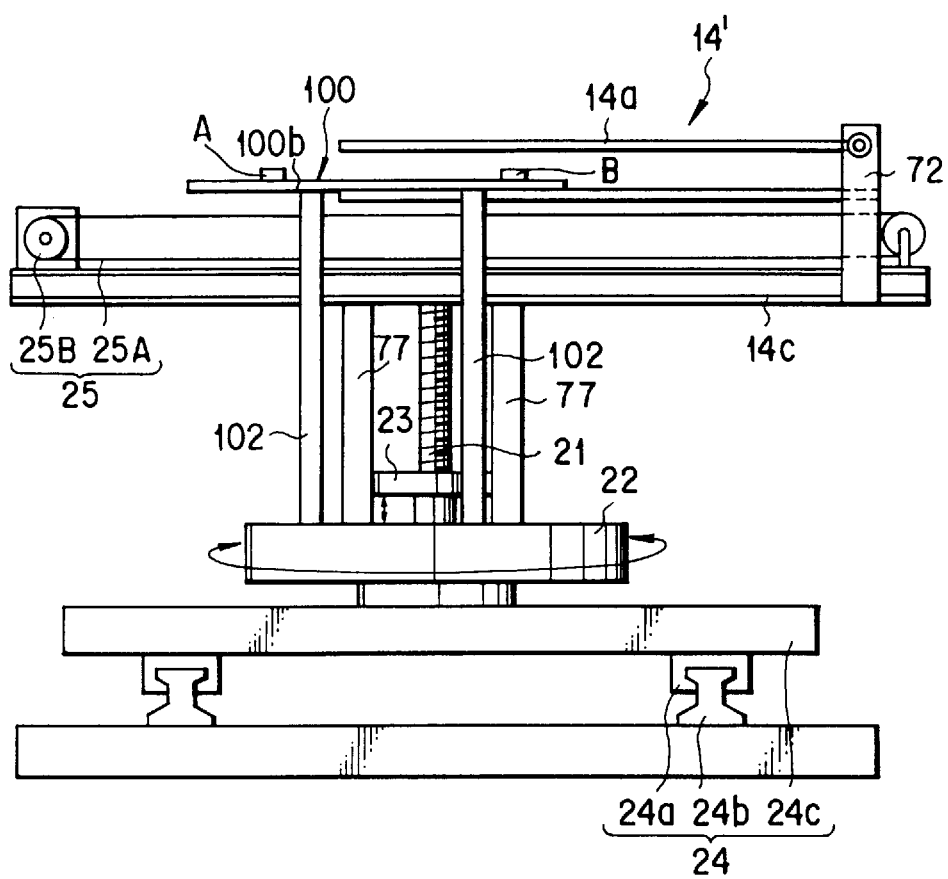
FIG. 7 is a side view, showing an LCD inspection apparatus according to another embodiment of the invention.

FIGS. 7 to 9 show another embodiment of the invention.

In a transfer unit 14' incorporated in this embodiment, the line sensors A, B and C and the disturbance light-detecting cell D are provided not on two arms 14a and 14b but on a sensor base 100 fixed to the base table 22. The sensor base 100 comprises two base portions 100a and 100b each supported by a plurality of support poles 102 fixed to the base table 22, on which base portions the LCD substrate S is to be mounted. A plurality of suction holes 31a are formed in the upper surfaces of the base portions 100a and 100b for holding thereon the LCD substrate S by a suction force. The two arms 14a and 14b are shaped as shown in FIG. 9, and each have a free end with a cutout 106 formed so as not to interrupt the vertical movement of the mount member 23. The other portions of the transfer unit 14 are identical to those of the transfer unit 14 shown in FIGS. 2 and 3.

In the above structure, the LCD substrate S is taken out of the cassette C1 by means of the arm 14a (14b) which moves above the sensor base 100, and then transferred from the arm 14a (14b) to the sensor base 100 by means of the mount member 23. Thereafter, the LCD substrate S has its position detected by the line sensors A, B and C and the disturbance light-detecting cell D on the sensor base 100, and has its displacement from a predetermined reference position corrected in the same manner as described above. In other words, in this embodiment, the correction performed on the arm 14a (14b) in the case of the structure shown in FIGS. 2 and 3 is performed on the sensor base 100. More specifically, the inclination angle θ of the LCD substrate S with respect to the Y-axis direction is corrected by the rotation of the mount member 23, and the Y-directional and X-directional displacements of the LCD substrate S are corrected by the movement of the mount table 23 and the arm 14a (14b).

Although in the embodiment, the transfer unit 14 is used in the probe apparatus 12 for inspecting the LCD substrate S, it is a matter of course that the unit 14 may be also used in any other apparatus (e.g. a semiconductor treatment apparatus) for inspecting or treating a large-scaled object such as the LCD substrate S.

Additional advantages and modifications will readily occur to those skilled in the art. Therefore, the invention in its broader aspects is not limited to the specific details, representative devices, and illustrated examples shown and described herein. Accordingly, various modifications may be made without departing from the spirit or scope of the general inventive concept as defined by the appended claims and their equivalents.

What is claimed is:

1. A transfer unit for transferring an object to an inspection position, comprising:

at least one transfer member movable between a standby position in which the object is in a standby state, and the inspection position in which the object is inspected, and having a support surface on which the object is mounted;

first fixing means provided at the support surface of the transfer member for fixing the object on the support surface;

detection means provided at the transfer member for detecting the position of the object on the support surface;

a rotatable mount member having a mount surface on which the object is mounted, and capable of transferring the object between the mount surface and the support surface of the transfer member;

second fixing means provided at the mount surface of the mount member for fixing the object on the mount surface; and control means for calculating an amount of deviation of the object from a reference position on the basis of a detection value of the detection means, with the object fixed on the support surface of the transfer member by means of the first fixing means, the control means also driving the mount member and the transfer member to correct the amount of deviation of the object from the reference position on the basis of the calculation result, with the object held on one of the support surface of the transfer member and the mount surface of the mount member by means of a corresponding one of the first and second fixing means, thereby situating the object in the reference position, wherein the detection means includes a plurality of detectors provided at those peripheral portions of the support surface of the transfer member and are located around an object-mounting portion of the surface, and wherein the detectors are arranged in two lines which intersect each other, and the calculation means calculates an angle defined between each of the two lines and a corresponding edge of the object, and amounts of deviation of the object from the reference position in the directions of the two lines.

2. The transfer unit according to claim 1, wherein the control means rotates the mount member with the object held on the mount surface of the mount member, in order to correct the angle defined between each of the two lines and a corresponding edge of the object.

3. The transfer unit according to claim 1, wherein the control means horizontally moves the transfer member in the direction of one of the two lines with the object held on the mount surface of the mount member, in order to correct the amount of deviation of the object from the reference position in the direction of each of the two lines.

4. A transfer unit for transferring an object to an inspection position, comprising:

at least one transfer member movable between a standby position in which the object is in a standby state, and the inspection position in which the object is inspected, and having a support surface on which the object is mounted;

first fixing means provided at the support surface of the transfer member for fixing the object on the support surface;

detection means provided at the transfer member for detecting the position of the object on the support surface;

a rotatable mount member having a mount surface on which the object is mounted, and capable of transferring the object between the mount surface and the support surface of the transfer member;

second fixing means provided at the mount surface of the mount member for fixing the object on the mount surface; and control means for calculating an amount of deviation of the object from a reference position on the basis of a detection value of the detection means, with the object fixed on the support surface of the transfer member by means of the first fixing means, the control means also driving the mount member and the transfer member to correct the amount of deviation of the object from the reference position on the basis of the calculation result, with the object held on one of the support surface of the transfer member and the mount surface of the mount member by means of a corresponding one of the first and second fixing means, thereby situating the object in the reference position, wherein the detection means has at least a sensor under a peripheral portion of the object held on the support surface of the transfer member, for detecting that part of ambient light applied to the object, which is reflected from a peripheral portion of the object, thereby detecting the position of the object, wherein the detection means includes a plurality of detectors provided at those peripheral portions of the support surface of the transfer member and are located around an object-mounting portion of the surface, and wherein the detectors are arranged in two lines which intersect each other, and the calculation means calculates an angle defined between each of the two lines and a corresponding edge of the object, and amounts of deviation of the object from the reference position in the directions of the two lines.

5. A transfer unit for transferring an object to an inspection position, comprising:

at least one transfer member movable between a standby position in which the object is in a standby state, and the inspection position in which the object is inspected, and having a support surface on which the object is mounted;

first fixing means provided at the support surface of the transfer member for fixing the object on the support surface;

detection means provided at the transfer member for detecting the position of the object on the support surface;

a rotatable mount member having a mount surface on which the object is mounted, and capable of transferring the object between the mount surface and the support surface of the transfer member;

second fixing means provided at the mount surface of the mount member for fixing the object on the mount surface; and control means for calculating an amount of deviation of the object from a reference position on the basis of a detection value of the detection means, with the object fixed on the support surface of the transfer member by means of the first fixing means, the control means also driving the mount member and the transfer member to correct the amount of deviation of the object from the reference position on the basis of the calculation result, with the object held on one of the support surface of the transfer member and the mount surface of the mount member by means of a corresponding one of the first and second fixing means, thereby situating the object in the reference position, wherein the detection means includes at least a sensor consisting of a plurality of cells with a size of 10–50 microns, wherein the detection means includes a plurality of detectors provided at those peripheral portions of the support surface of the transfer member and are located around an object-mounting portion of the surface, and wherein the detectors are arranged in two lines which intersect each other, and the calculation means calculates an angle defined between each of the two lines and a corresponding edge of the object, and amounts of deviation of the object from the reference position and the directions of the two lines.

6. A transfer unit for transferring an object to an inspection position, comprising:

at least one transfer member movable between a standby position in which the object is in a standby state, and the inspection position in which the object is inspected, and having a support surface on which the object is mounted;

first fixing means provided at the support surface of the transfer member for fixing the object on the support surface;

detection means Provided at the transfer member for detecting the position of the object on the support surface;

a rotatable mount member having a mount surface on which the object is mounted, and capable of transferring the object between the mount surface and the support surface of the transfer member;

second fixing means provided at the mount surface of the mount member for fixing the object on the mount surface;

control means for calculating an amount of deviation of the object from a reference position on the basis of a detection value of the detection means, with the object fixed on the support surface of the transfer member by means of the first fixing means, the control means also driving the mount member and the transfer member to correct the amount of deviation of the object from the reference position on the basis of the calculation result, with the object held on one of the support surface of the transfer member and the mount surface of the mount member by means of a corresponding one of the first and second fixing means, thereby situating the object in the reference position; and disturbance light detection means provided on the transfer member for detecting disturbance light generated from an element other than the object.

7. The transfer unit according to claim 6, wherein the control means corrects a detection value output from the detection means, on the basis of a detection value output from the disturbance light detection means.

8. A transfer unit for transferring an object to an inspection position, comprising:

at least one transfer member movable between a standby position in which the object is in a standby state, and the inspection position in which the object is inspected, and having a support surface on which the object is mounted;

first fixing means provided at the support surface of the transfer member for fixing the object on the support surface;

detection means provided at the transfer member for detecting the position of the object on the support surface;

a rotatable mount member having a mount surface on which the object is mounted, and capable of transferring the object between the mount surface and the support surface of the transfer member;

second fixing means provided at the mount surface of the mount member for fixing the object on the mount surface; and control means for calculating an amount of deviation of the object from a reference position on the basis of a detection value of the detection means, with the object fixed on the support surface of the transfer member by means of the first fixing means, the control means also driving the mount member and the transfer member to correct the amount of deviation of the object from the reference position on the basis of the calculation result, with the object held on one of the support surface of the transfer member and the mount surface of the mount member by means of a corresponding one of the first and second fixing means, thereby situating the object in the reference position, wherein the first and second fixing means fix the object on the support surface of the transfer member and on the mount surface of the mount member by suction forces, respectively.

9. A transfer unit for transferring an object to an inspection position, comprising:

at least one transfer member movable between a standby position in which the object is in a standby state, and the inspection position in which the object is inspected, and having a support surface on which the object is mounted;

first fixing means provided at the support surface of the transfer member for fixing the object on the support surface;

detection means provided at the transfer member for detecting the position of the object on the support surface;

a rotatable mount member having a mount surface on which the object is mounted, and capable of transferring the object between the mount surface and the support surface of the transfer member;

second fixing means provided at the mount surface of the mount member for fixing the object on the mount surface; and control means for calculating an amount of deviation of the object from a reference position on the basis of a detection value of the detection means, with the object fixed on the support surface of the transfer member by means of the first fixing means, the control means also driving the mount member and the transfer member to correct the amount of deviation of the object from the reference position on the basis of the calculation result, with the object held on one of the support surface of the transfer member and the mount surface of the mount member by means of a corresponding one of the first and second fixing means, thereby situating the object in the reference position, wherein the control means calculates, on the basis of detection values of the detection means, angular deviation of the object from the reference position in the direction of rotation of the mount member, and amounts of deviation of the object from the reference position in two directions intersecting each other at right angles, and the control means rotates the mount member by an angle corresponding to the angular deviation, and horizontally moves the transfer member by a corresponding amount of deviation in the direction of one of the two lines, with the object held on the mount surface of the mount member, thereby situating the object in the reference position.

10. A transfer unit for transferring an object to an inspection position, comprising:

at least one transfer member movable between a standby position in which the object is in a standby state, and the inspection position in which the object is inspected, and having a support surface on which the object is mounted;

first fixing means provided at the support surface of the transfer member for fixing the object on the support surface;

a support member with an upper surface on which the object is mounted;

detection means provided on the transfer member for detecting the position of the object on the upper surface of the support member;

second fixing means provided at the upper surface of the support member for fixing the object thereon;

a rotatable mount member having a mount surface on which the object is mounted, and capable of transferring the object between the mount surface and one of the support surface of the transfer member and the upper surface of the support member;

third fixing means provided at the mount surface of the mount member for fixing the object on the mount surface; and control means for calculating an amount of deviation of the object from a reference position on the basis of a detection value of the detection means, with the object fixed on the upper surface of the support member by means of the second fixing means, the control means also driving the mount member and the transfer member to correct the amount of deviation of the object from the reference position on the basis of the calculation result, with the object held on one of the support surface of the transfer member, the upper surface of the support member and the mount surface of the mount member by means of a corresponding one of the first through third fixing means, thereby situating the object in the reference position.

11. A method for transferring an object to an inspection position, comprising the steps of:

moving a transfer member to a standby position and mounting, in a fixed manner, the object set in the standby position, to the support surface of the transfer member;

detecting the position of the object held on the support surface of the transfer member at the time of moving the transfer member to transfer the object from the standby position, and calculating, on the basis of a detection result, an amount of angular deviation of the object from a reference position, and amounts of deviation of the object from the reference position in two directions intersecting each other at right angles;

mounting the object fixed on the support surface of the transfer member, on the mount surface of a rotary member in a fixed manner, then releasing the fixing state of the object on the support surface of the transfer member, rotating the rotary member through an angle corresponding to the calculated amount of angular deviation of the object from the reference position, with the object fixed on the mount surface of the rotary member and separated from the transfer member, thereby correcting the angular deviation of the object from the reference position;

horizontally moving the transfer member in one of the two directions by the calculated amount of deviation of the object from the reference position in the one of the two directions, then mounting, on the support surface of the transfer member in a fixed manner, the object fixed on the mount surface of the rotary member and having its angular deviation from the reference position corrected, and releasing the fixed state of the object on the mount surface of the rotary member to separate the object from the rotary member while keeping the object fixed on the transfer member;

mounting the object fixed on the support surface of the transfer member, on the mount surface of a rotary member in a fixed manner, then releasing the fixing state of the object on the support surface of the transfer member, rotating the rotary member through 90° with the object fixed on the mount surface of the rotary member and separated from the transfer member, horizontally moving the transfer member in the one of the two directions intersecting each other by the calculated amount of deviation of the object from the reference position in the other of the two directions, mounting the object fixed on the mount surface of the rotary member, on the support surface of the transfer member in a fixed manner, and releasing the fixing state of the object on the mount surface of the rotary member to separate the object from the rotary member while keeping the object fixed on the transfer member; and transferring, by the transfer member to the inspection position, the object having its amount of angular deviation from the reference position corrected also having its amounts of deviation from the reference position in the two directions corrected, and accordingly situated in the reference position.

\* \* \* \* \*